United States Patent [19]
Tu et al.

[11] Patent Number: 5,997,534
[45] Date of Patent: Dec. 7, 1999

[54] MEDICAL ABLATION DEVICE AND METHODS THEREOF

[76] Inventors: Hosheng Tu; Lily Chen Tu, both of 2151 Palermo, Tustin, Calif. 92782

[21] Appl. No.: 09/093,586

[22] Filed: Jun. 8, 1998

[51] Int. Cl.⁶ .................................................. A61B 17/39
[52] U.S. Cl. .............................. 606/41; 606/41; 606/47; 607/102
[58] Field of Search ................... 606/41–50, 11, 606/170, 171, 180; 607/102

[56] References Cited

U.S. PATENT DOCUMENTS

| | | | |
|---|---|---|---|
| 5,527,331 | 6/1996 | Kresch et al. ........................... | 606/170 |
| 5,728,143 | 3/1998 | Gough et al. ........................... | 607/101 |
| 5,733,277 | 3/1998 | Pallarito ..................................... | 606/7 |
| 5,810,804 | 9/1998 | Gough et al. ........................... | 606/41 |
| 5,904,681 | 5/1999 | West, Jr. .................................. | 606/41 |

*Primary Examiner*—Linda C. M. Dvorak
*Assistant Examiner*—David M. Ruddy

[57] ABSTRACT

A medical ablation device system for treating endometrosis, gingivae or reducing the mass of cellular tissue, wherein an elongate tubular element comprises an electrode means disposed at its distal section, the energy generating means, and means for generating rotational sweeping force at the distal section of the tubular element to effect the heat treatment and the rotational sweeping massage therapy for the target tissue.

7 Claims, 10 Drawing Sheets

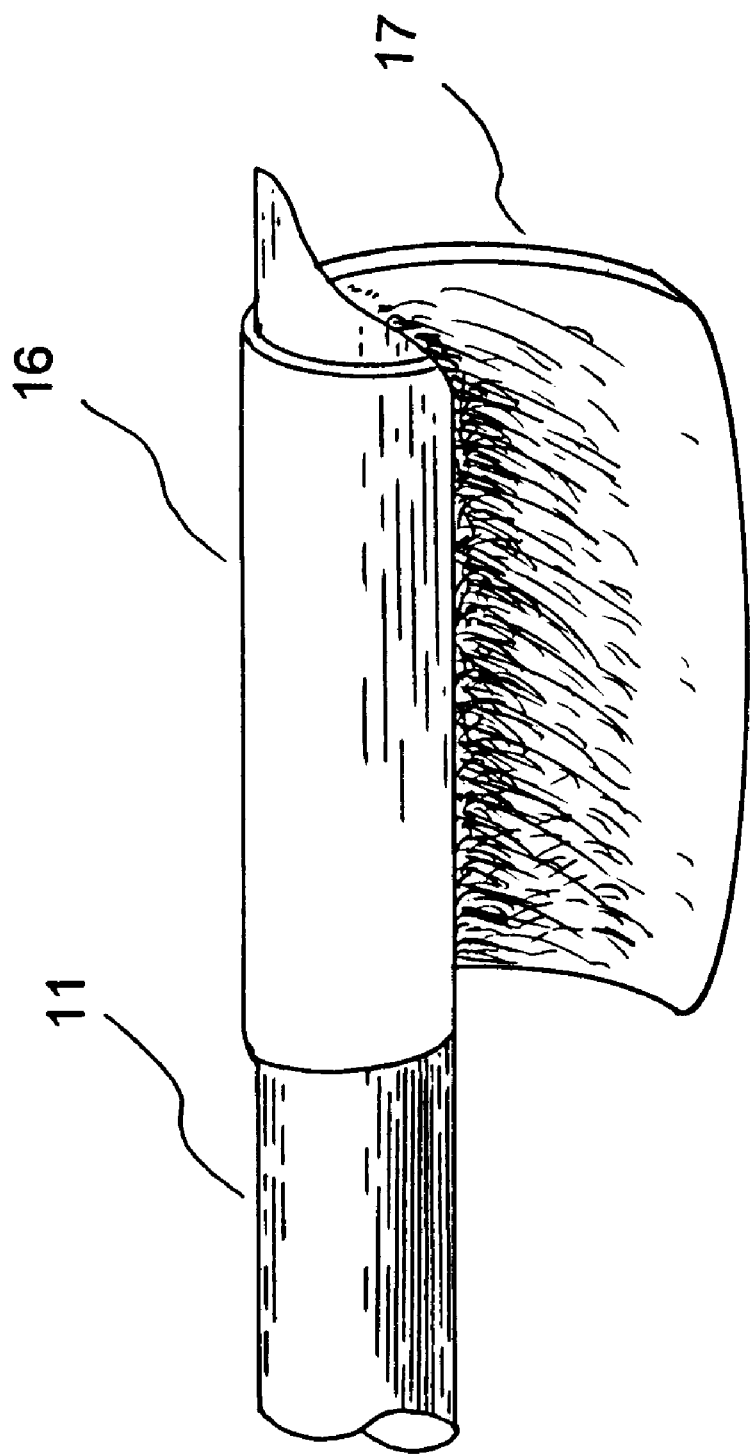
FIG. 4-A

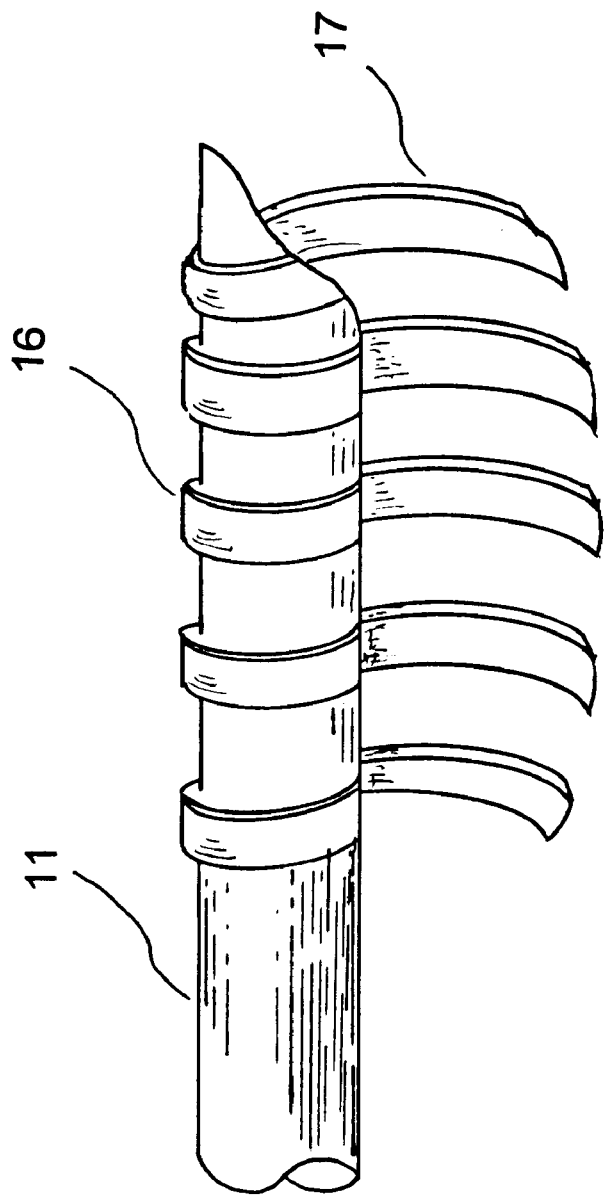
FIG. 4-B

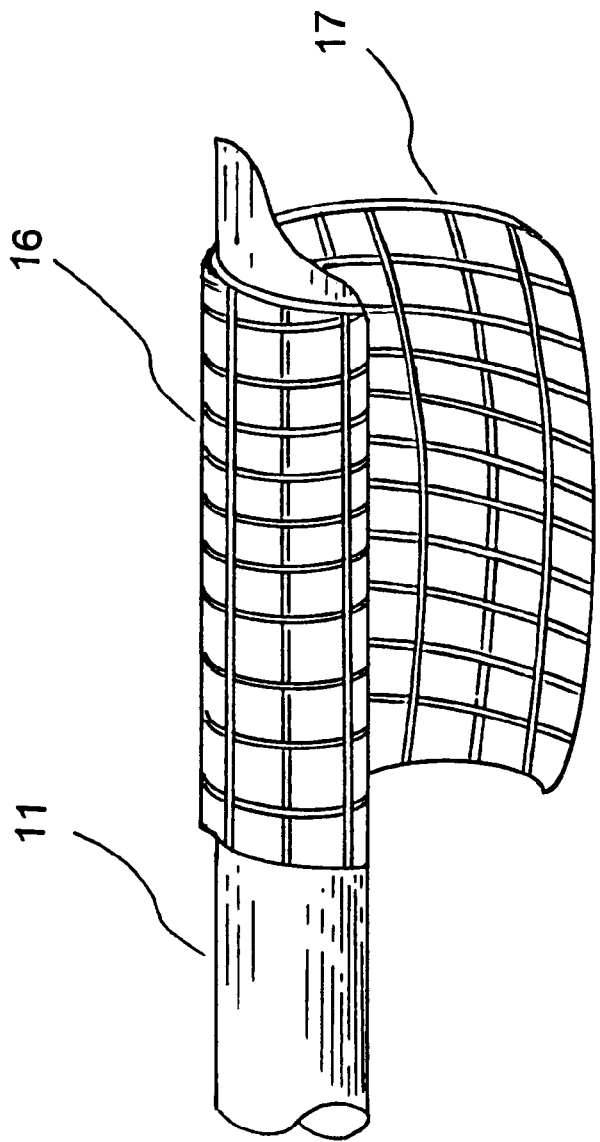
FIG. 4-C

MEDICAL ABLATION DEVICE AND METHODS THEREOF

The present invention generally relates to an improved device and methods for medical purposes, and more particularly, to such a device and methods for providing appropriate heat treatment in a patient by delivering thermal energy to an endometrosis site, or other tissues, and a simultaneously continuous sweeping massage therapy.

BACKGROUND OF THE INVENTION

Endometrosis is a condition in which fragments of the lining of the uterus spread to other tissues, such as the wall of the uterus, the ovaries, the peritoneum, or the bowel. The causes of the disease are unknown, but its incidence is higher in women who defer pregnancy. The fragments are benign, but may cause complications if they lodge in a critical location, leading to an organ dysfunction.

There is no definite symptoms of endometrosis, and the condition is found only during a surgical operation for other disorders. When endometrosis is present, symptoms include heavy periods, often more frequent than usual, accompanied by pain (dysmenorrhea); pain during sexual intercourse (dyspareunia); sometimes infertility; and sometimes pain on defecation during a period. The abnormally placed fragments of endometrium pass through the same monthly cycle as does the normal endometrium. They swell before a period and then bleed. Because there is no outlet for the blood, cysts form. These cysts occasionally rupture, causing severe abdominal pain.

In milder cases, painkilling drugs may lesson the symptoms. However, in severe cases, surgery or laser treatment are currently the only two options. As one of the severe cases, cul-de-sac obliteration implies the presence of retrocervical deep fibrotic endometrosis. The deep fibrotic endometrosis is usually located on the upper vagina, on the superficial anterior rectum, in the rectovaginal space, in the space between the upper vagina and the cervix (cervicovaginal angle), or in one or both uterosacral ligaments. With deep cul-de-sac obliteration, fibrotic endometrosis or adhesions sometimes involve the entire area between the cervicovaginal junction and the rectovaginal septum.

Surgery exposes a patient to greater risks, due to infection and other health reasons. The laser culdotomy, a procedure for the removal of cul-de-sac obliteration, poses a risk of unwanted tissue perforation or tissue vaporization. A less invasive approach using RF therapeutic protocols, has been proven to be highly effective when used by electrophysiologists for the treatment of tachycardia; by neurosurgeons for the treatment of Parkinson's disease; and by neurosurgeons and anesthetists for other RF procedures such as Gasserian ganglionectomy for trigeminal neuralgia and percutaneous cervical cordotomy for intractable pains. Radiofrequency treatment, when coupled with a temperature control mechanism, can supply precise energy to the device-to-tissue contact site to obtain the desired thermal energy for treatment.

To be more efficient in RF energy ablations, the electrode with a rotational sweeping capability to cover the broad area is used to simultaneously deliver the sweeping massage therapy to the target tissue. Edwards et al. in U.S. Pat. No. 5,456,662 entitled "Method for reducing snoring by RF ablation of the uvula" teaches a medical ablation method for reducing snoring wherein a flexible RF electrode wire is inserted into the uvula, and RF energy is applied to the uvula tissue to cause internal lesions. However, Edwards et al. does not disclose a device to ablate tissues, in which there is the capability for simultaneously delivering radiofrequency energy and rotational sweeping massage therapy.

Therefore, there is a need for an improved medical device and methods using radiofrequency energy to treat the endometrosis or tumors, while applying rotational sweeping massage therapy.

SUMMARY OF THE INVENTION

In general, it is an object of the present invention to provide a method and an improved medical ablation device for generating heat, to treat endometrosis, cysts, polyps, prostate, tumors, or cellular tissues. It is another object of the present invention to provide a device in which rotational sweeping massage therapy is applied to the endometrosis, cysts, polyps, prostate, tumors, or the target cellular tissues, for intimate contact. The "rotational sweeping massage" in this invention implies that the surface of a rotational device (e.g., a plate-like electrode or a cam-type electrode) continuously or intermittently contacts a target tissue with a normal sweeping force by said rotational device. The "target tissue" in this invention indicates the endometrosis, the cysts, the gingivae, the tumor, the prostate, the polyp or other cellular tissues.

It is another object of the present invention to provide a method and a device for monitoring the temperature of the medical device, and to control the temperature by utilizing a temperature control mechanism and/or algorithm. The location of the temperature sensor means is preferably at the proximity of the tip portion of the medical device. It is still another object of this invention to provide methods and a device for treating the endometrosis, cysts, polyps, prostate, tumors, or cellular tissues in a patient by delivering a therapeutic agent to the target site.

Briefly, beat is generated by applying a suitable energy source to a device, which comprises an electrode means, in contact with the body tissue. A suitable energy source may consist of radiofrequency energy, microwave energy, ultrasonic energy, alternating current energy, or laser energy. The energy is applied to the endometrosis, cysts, canker sore, gingivae, polyps, tumors, prostate, or other cellular tissues through the electrode means. A DIP (dispersive indifferent pad) type electrode, that contacts the patient, is connected to the Indifferent Electrode Connector on the RF generator. When using an alternating current electrical outlet, the generator should be grounded to avoid electrical interference. Heat is controlled by the power of the RF energy being delivered and by the delivery duration. The standard RF energy generator means, and its applications through the electrode means to a patient, are well known for those who are skilled in the art.

In a further embodiment, means for generating rotational motion for the distal section of the elongate tubular element of the catheter system comprises a motor mounted in a cavity of the handle, which has a rotatable motor shaft, an elongate connecting shaft having a first end to which the proximal end of the elongate tubular element is connected, and a second end connected to the motor, so that when the motor shaft rotates, the elongate tubular element also rotates.

In one embodiment, the device is leak-proof so that the therapeutic agent, in either fluid phase or gel phase, is forced under a positive pressure to flow inside the lumen of the medical device from its proximal end to the distal end. The fluid is vented through an opening at the proximity of the electrode means to effect the therapeutic purposes to the target tissue site.

The methods and device of the present invention have several significant advantages over other known systems or techniques to treat the endometrosis, the cysts, the canker sore, the gingivae, the polyps, the prostate, the tumors, or other cellular tissues. In particular, the device system comprising the electrode means, using RF energy as a heat source, in this invention, and simultaneously delivering rotational sweeping massage therapy to the target tissue sites, results in a more efficient therapeutic effect, which is highly desirable in its intended application on treating the endometrosis, cysts, canker sores, gingivae, polyps, tumors, prostate, other cellular tissues, or other medical applications.

BRIEF DESCRIPTION OF THE DRAWINGS

Additional objects and features of the present invention will become more apparent and the invention itself will be best understood from the following Detailed Description of Exemplary Embodiments, when read with reference to the accompanying drawings.

FIG. 4-A is a perspective view of the electrode means, which is a pre-shaped curved plate.

FIG. 4-B is a perspective view of the electrode means, which include a plurality of pre-shaped curved wires.

FIG. 4-C is a perspective view of the electrode means, which is a pre-shaped curved mesh.

DETAILED DESCRIPTION OF EXEMPLARY EMBODIMENTS

Figure 1:
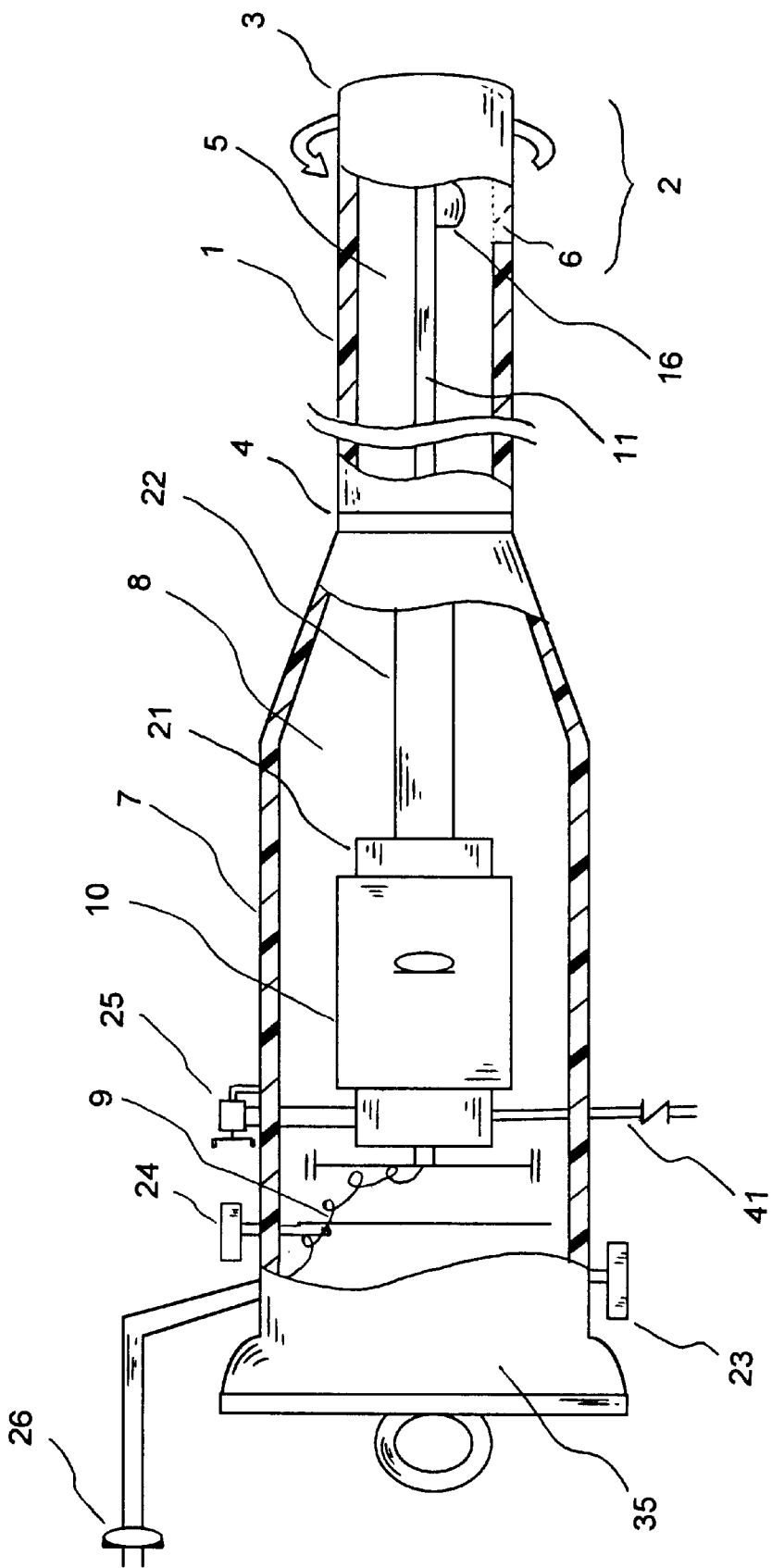
FIG. 1 is an overall view of the medical device, having an electrode means with heat generating source and a rotation generating means, constructed in accordance with the principles of the present invention.

Referring to FIGS. 1 to 8, what is shown is an embodiment of a medical ablation device system, comprising simultaneously applying radiofrequency energy and applying a rotational sweeping therapeutic massage to treat the endometrosis, cysts, gingivae, tumors, prostate, polyps, or cellular tissues of a patient. As shown in FIG. 1, a medical ablation device system comprises an elongate tubular element 1 having a distal section 2, a distal end 3, a proximal end 4, and at least one lumen 5 extending therebetween, wherein an opening 6 is located at one side of the distal section 2. An inner tubing 11 is located within the lumen 5 of the elongate tubular element 1. The inner tubing 11 has a distal section 12, a distal end 13, a proximal end 14, and a lumen 15 extending therebetween, wherein a deployable electrode 16 is located at the distal section 12 of the inner tubing 11. The deployable electrode means 16 comprises a pre-shaped extendible electrode 17 that stays within the lumen of the elongate tubular element 1 under a non-deployed state and extends out of the elongate tubular element 1 through said opening 6 during a deployed state.

A handle 7 is attachably secured at the proximal end 4 of the tubular element 1. The handle 7 has a cavity 8. An external RF energy generator (not shown) has a conducting wire 9, wherein the RF energy is supplied to the deployable electrode means 16 through the conducting wire 9. The RF energy supply is controlled by an on-off switch button 24 located conveniently on the handle 7.

The medical ablation device system further comprises means for generating rotational motion for the distal section of the elongate tubular element 1. The means comprises a motor 10 mounted in the cavity 8 of the handle 7, which has a rotatable motor shaft 21 connected to an elongate connecting shaft 22 having a first end to which the proximal end 4 of the elongate tubular element 1 is coupled and connected, and a second end connected to the motor 10, so that when the motor shaft 21 rotates, the elongate tubular element 1 also rotates. The handle 7 is also equipped with an on-off electrical controller 23 for the motor 10, an on-off controller 24 for the RF energy delivery conducting wire 9, a connector 26, and an engagement controller 25 which is used to control the extending degree of the extendible electrode 17, either inside the elongate tubular element 1 or out of the opening 6 of the elongate tubular element 1.

In one embodiment, a battery means 35, which is located at the proximal end of the cavity 8 of the handle 7, is used to supply the energy to the motor 10. In an alternate embodiment, the motor 10 is powered by an alternating current (AC) through a power input plug (not shown). In either case, the power supply is controlled by an on-off switch button 23 located conveniently at the proximal end of the handle 7.

Figure 2:
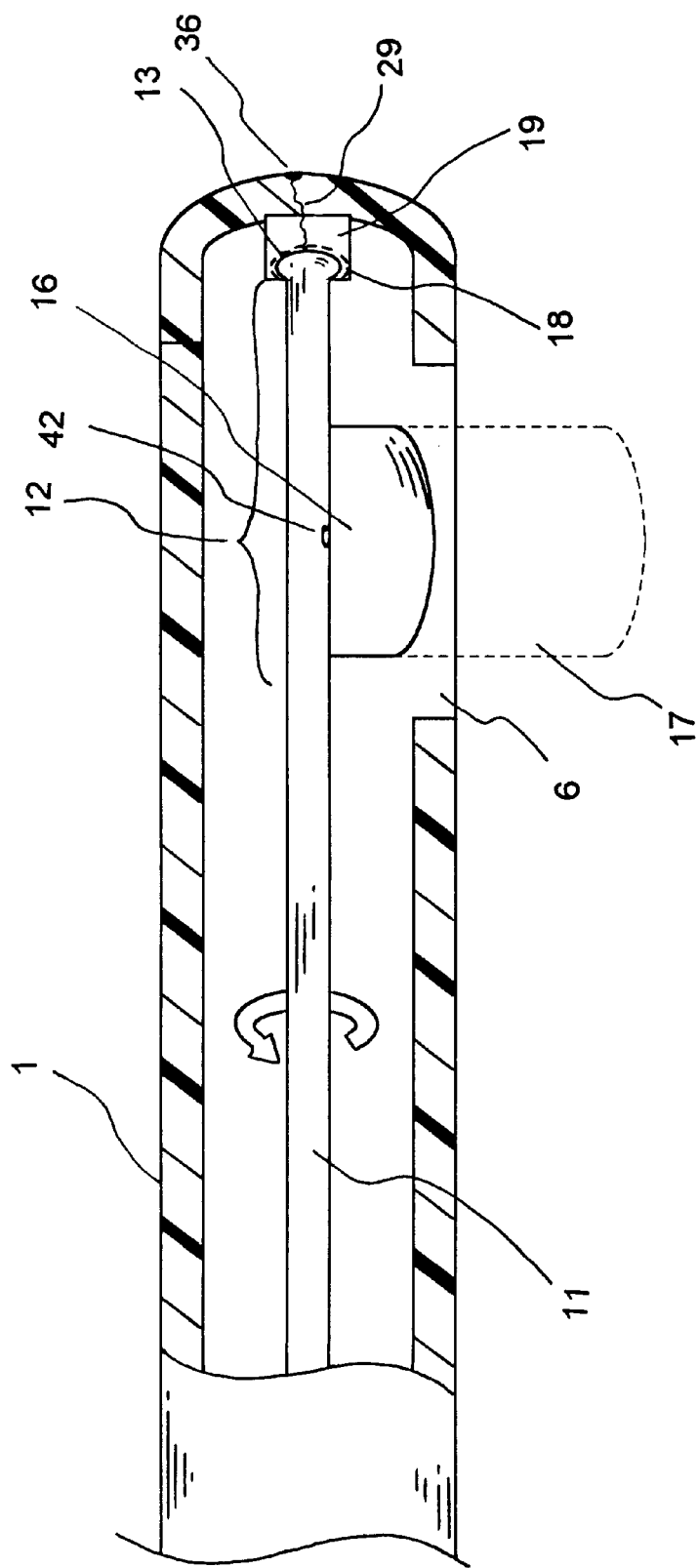
FIG. 2 is a cross-sectional view of the distal portion of the medical device in FIG. 1.

FIG. 2 shows a cross-sectional view of the distal portion of the medical device in FIG. 1. The inner tubing 11 has a deployable electrode means 16 comprising a pre-shaped extendible electrode 17, and a distal end 13, wherein the distal end 13 is securely suspended inside a cavity 18 of an attachment member 19. The attachment member 19 is secured to the inner side of the distal end 3 of the elongate tubular element 1. The inner tubing 11 is rotatable relative to the elongate tubular element 1 in either direction, of which direction dictates the deployment and un-deployment states of the extendible electrode 17 from the deployable electrode means 16. After deployment of the extendible electrode, the inner tubing 11 and the elongate tubular element 1 are locked together as one unit and adapted to be rotatable by the movement of the motor shaft 21.

In one preferred embodiment, the very distal end 3 of the elongate tubular element 1 is shaped as a needle so that the distal end can be inserted into the tissue to stabilize the medical ablation device system for ablative operations.

Figure 3:
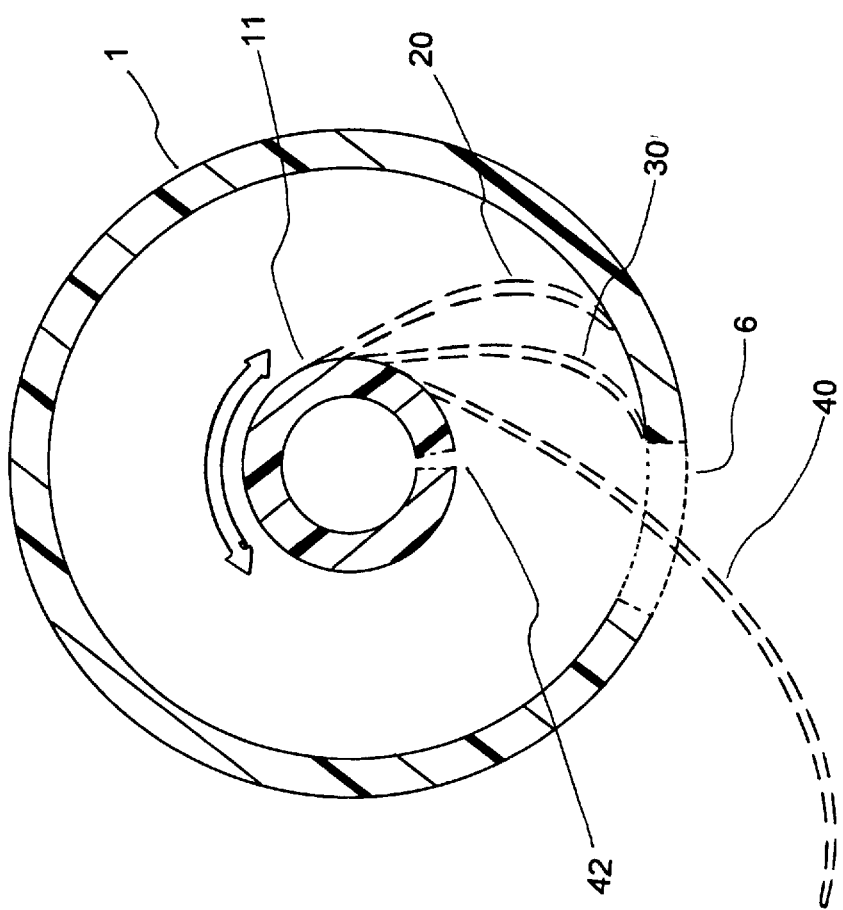
FIG. 3 is a transverse view of the electrode means, including an extendible electrode.

The window dimensions of the opening 6 of the elongate tubular element 1 are such that the extendible electrode 17 is free to deploy and un-deploy without undue obstruction. FIG. 3 shows a transverse view of the electrode means 16, including an extendible electrode 17. The extendible electrode 17 can be adjusted in several different deployment states, such as the non-deploy state 20, the ready-to-deploy state 30, and fully deployed state 40.

FIG. 4 A–C show some of the perspective views of the deployable electrode means. The extendible electrode 17 may be selected from the group consisting of a curved plate, a plurality of curved wires, a curved plate with studded surface, a plurality of coils, a meshed plate, and the like. Because of its pre-shaped memory and material strength, the curved electrode 17 is advanced out of the opening 6 during deployment phase. As shown in FIG. 3, the elongate tubular element 1 should be rotated in the same direction as the extendible electrode; in this case, the counter-clockwise direction to effect the rotational sweeping massage therapy to the target tissue.

Figure 5:
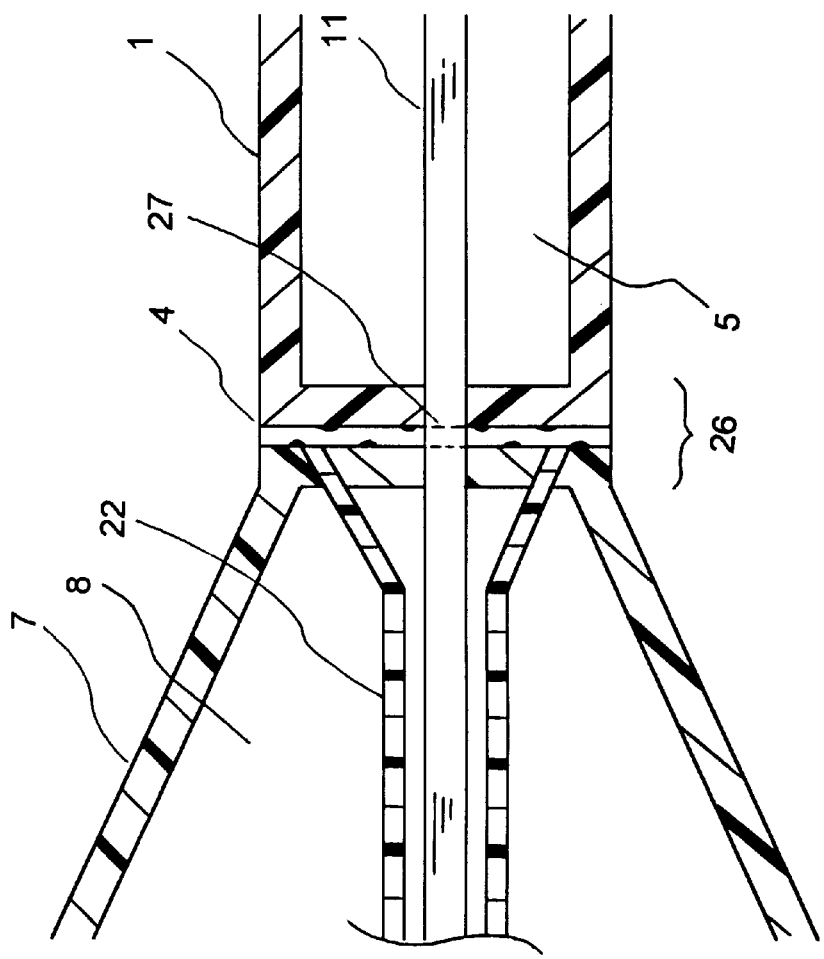
FIG. 5 is a cross-sectional view of a coupling mechanism between an elongate tubular element of the medical device and a handle portion.
Figure 6:
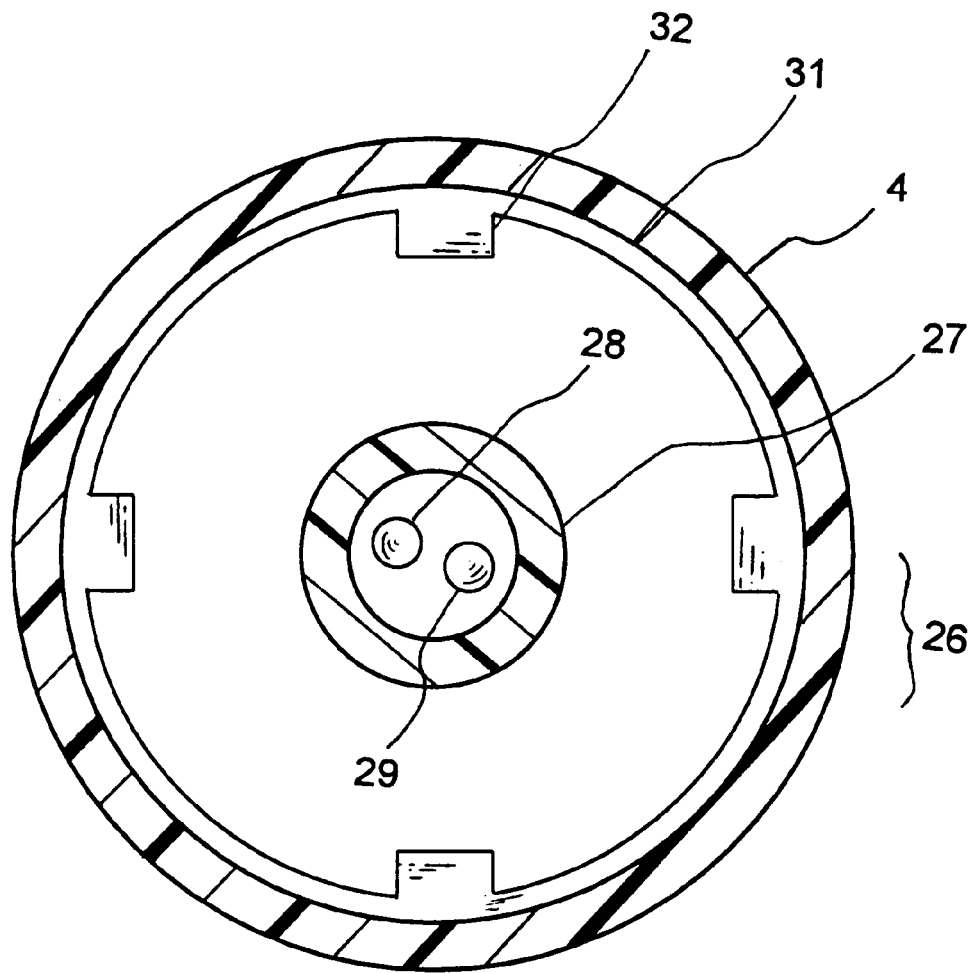
FIG. 6 is a transverse view of the coupling mechanism of FIG. 4.

FIG. 5 shows a cross-sectional view of the coupling mechanism between an elongate tubular element 1 of the medical device and a handle portion 7. The coupling mechanism 26 comprises two members: the distal tubular portion and the proximal handle portion of the medical ablation device system. The proximal handle portion of the coupling mechanism 26 is secured to the elongate connecting shaft 22, wherein the elongate connecting shaft is connected to the motor shaft 21. The distal tubular portion includes a proximal end 4 of the tubular element 1, a first transitional end 27 of the inner tubing 11, a first conducting wire 28 for the RF energy delivery, a first temperature sensing wire 29 for the optional temperature sensors, and a locking groove 31 with a plurality of locking elements 32. The proximal handle portion includes their corresponding matching ends on the other member of the coupling mechanism. FIG. 6 shows a transverse view of the coupling mechanism of FIG. 5. When coupled, the distal tubular portion of the device and the proximal portion (i.e., the handle) of the device becomes one unit. The distal tubular portion is thereafter rotatable with respective to the handle portion. When uncoupled, the first transitional end 27 of the inner tubing 11 and its counterpart of a second transitional end (not shown) of the proximal portion of the inner tubing, that is located inside the cavity 8 of the handle 7, is temporarily dissociated from the coupling mechanism 26. During the uncoupled phase, the inner tubing is free to rotate so that the extendible electrode 17 can be deployed or un-deployed.

Figure 7:
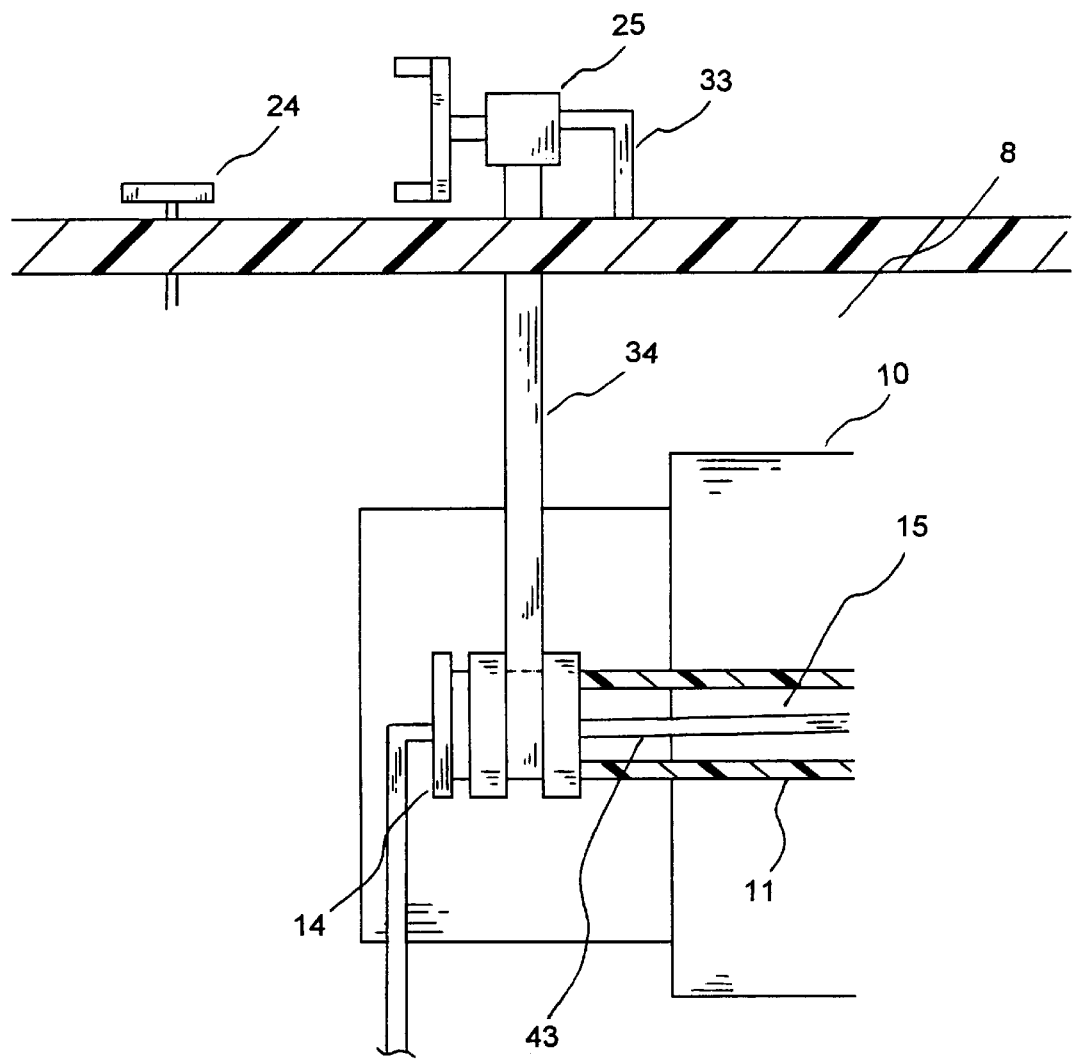
FIG. 7 is a cross-sectional view of a control mechanism of the inner tubing at its proximal portion.

FIG. 7 shows a cross-sectional view of a control mechanism of the inner tubing at its proximal portion. The proximal end 14 of the inner tubing 11 extends all the way to the handle portion. A conveying means 34, either a belt-type or chain-type, is used to connect the proximal portion 14 of the inner tubing 11 to an external controller 25. The engagement controller 25 is used to advance the extendible electrode 17 out of the opening 6 of the elongate tubular element 1 and/or retract it back to inside the lumen 5 of the tubular element 1. The engagement controller 25 is equipped with a level adjuster 33 so that the controller 25 is functional only when the coupling mechanism 26 is in the uncoupled state. In other words, the level adjuster 33 makes the engagement controller 25 non-functional when the coupling mechanism 26 is in the coupled state.

The extendible electrode is preferably selected from the group consisting of platinum, iridium, gold, silver, stainless steel, Nitinol, and an alloy of their mixtures. The outer surface of the medical device, except the electrode means at its distal portion, is not conductive. A conducting wire 9 is used to transmit the RF energy from the external RF generating means to the deployable electrode means 16. One end of the conducting wire 9 is secured and connected to the electrode means 16 at the distal section 2 while the other end of the conducting wire 9 is secured to a contact pin of the collector 26, wherefrom the conducting wire 9 is connected to an external RF generator means (not shown) or other energy source.

In one embodiment, a temperature sensing means 36 is disposed close to the electrode means 16. An insulated temperature sensor wire means 29 passes from the temperature sensing means 36 at the distal end, through the lumen 15 of the inner tubing 11, to an external temperature control mechanism through the outlet connector 26. The energy delivery is controlled by the measured temperature from the temperature sensing means 36, a closed-loop temperature control mechanism and/or an algorithm. When the measured temperature rises to the preset high-limit point, the temperature control mechanism sends out a signal to cut off the energy supply. In a similar manner, when the measured temperature drops to the preset low-limit point, the temperature control mechanism sends out a signal to activate the energy supply. The control mechanism can be a proportional mode, a derivative mode, an integral mode, or a combination of the above modes. The RF energy delivery can also be operated in a Power Control Mode, which is not controlled by any temperature factor.

In another embodiment, a fluid infusion means 41 is provided for the irrigation of a desired therapeutic agent, in either fluid phase or gel phase, to the enidometrosis site or to the target cellular tissue site. The fluid is adapted to diffuse out of the inner tubing 11 at an inner opening 42 at the proximity of the electrode means 16. The therapeutic agent is selected from the group consisting of heparin solution, saline solution, fluoroquinolone, lactic acid, glycolic acid, alpha hydroxy organic acids, vitamins, povidone-iodine, nitrate compounds, virucidal agents, anti-inflammatory agents, antibiotics and/or their mixtures. A passage 43 is provided inside the lumen of the inner tubing 11 for transporting the fluid or gel from the proximal end 14 of the inner tubing 11 to the distal end 13. Thereafter the fluid or gel is diffused out of the inner tubing 11 through the inner opening 42 and thereafter out of the tubular element 1 through the opening 6.

Figure 8:
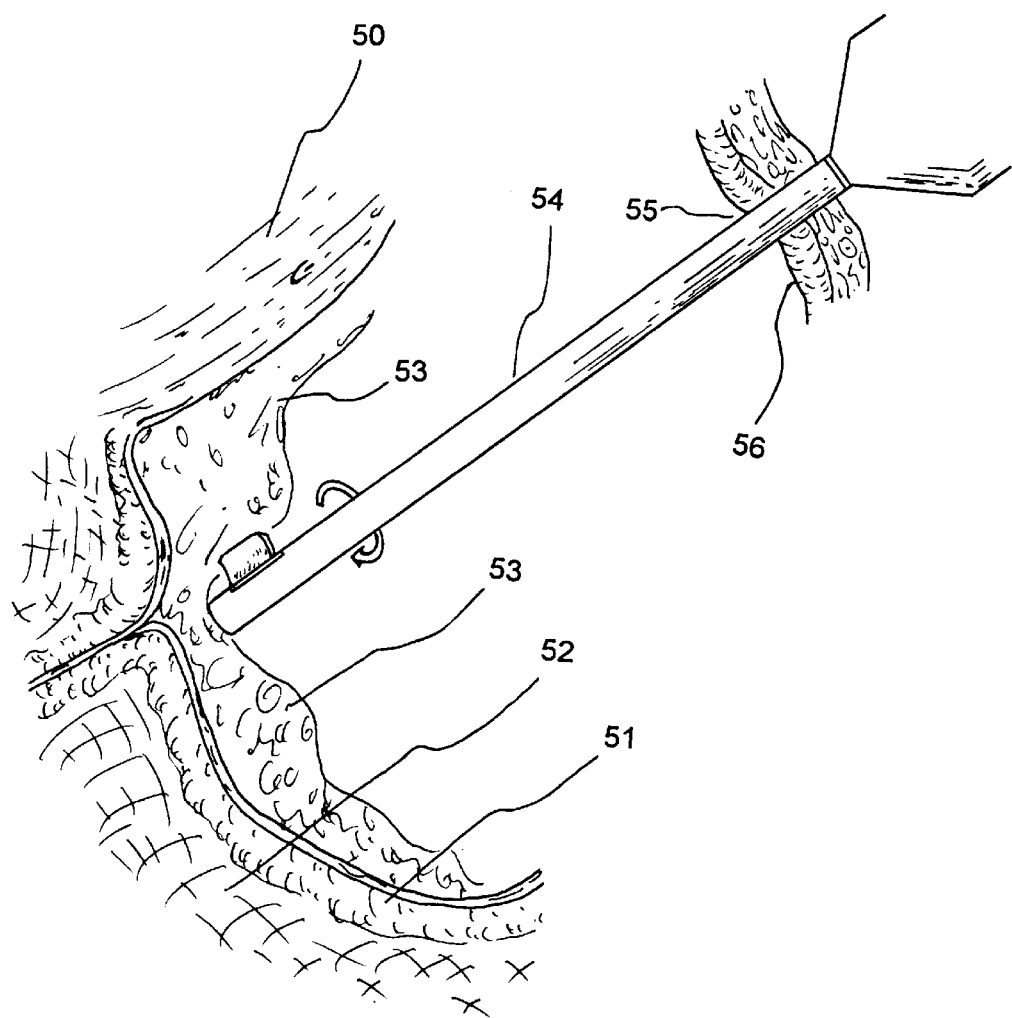
FIG. 8 is a simulated perspective view of the endometrosis being treated by the medical device of the present invention.

FIG. 8 shows a perspective view of the endometrosis being treated by the medical ablation device of the present invention. For illustration purposes, the uterus 50 of a patient is briefly shown here. The rectum 51 and the rectal wall 52 are at the lower part of FIG. 8, wherein the endometrosis 53 is shown at the exterior wall of the uterus 50. A medical ablation device 54 of the present invention is inserted through the puncture 55 of the skin 56, following a standard laparoscopic approach. To position the patient for a more effective ablation, the uterus may be optionally stretched anteriorly using a uterine elevator, while the rectum is retracted from the uterus and vagina by a rectal probe.

The distal end of the ablation device 54 is positioned against the wall of the rectum and uterine. Thereafter, the extendible electrode 17 is advanced out of the elongate tubular element 1 and the coupling mechanism 26 is activated. The device is now ready for RF energy ablation in association with the rotational sweeping massage therapy. Optionally, the fluid can be infused to effect the cooling of the electrode and for the therapeutic purposes. In one embodiment, the external RF energy generator means has the capability to supply RF energy by controlling the time, power, and temperature through an optional separate closed-loop temperature control means. The patient is connected to the RF generator means through a DIP electrode to form a closed-loop current system. Therefore, RF energy is applied and delivered to the target endometrosis site, through the electrode means 17 of this invention.

The radiofrequency energy current in this invention is preferably within the range of 50 to 2,000 kHz. The frequency of the vibration of the medical device in this invention is preferably within the range of 60 to 1000 cycles per minute. By simultaneously applying RF energy to the electrode means and applying the rotational sweeping massage therapy topically, the endometrosis disease can be treated.

A method for treating the endometrosis of a patient with a medical ablation device system comprises: inserting the medical ablation device system into the abdominal cavity of a patient using a standard laparoscopic technique; positioning the tip of the device system upon the wall of the abdominal cavity where an endometrosis prevails; deploying the extendible electrode out of the opening of the elongate tubular element of the device system; applying RF energy to the extendible electrode of the device system to effect heat treatment of the endometrosis.

In an alternate embodiment, the method for treating the endometrosis of a patient with a medical ablation device system comprises: inserting the medical ablation device system into the uterus of a patient using a standard inserting technique; positioning the tip of the device system upon the wall of the uterus where an endometrosis prevails; deploying the extendible electrode out of the opening of the elongate tubular element of the device system; applying RF energy to the extendible electrode of the device system to effect heat treatment of the endometrosis.

From the foregoing description, it should now be appreciated that a medical ablation device system for the endometrosis, cysts, gingivae, polyps, prostate, tumors, or cellular tissues treatment, comprising a suitable energy source and a rotational sweeping massage therapy, with an optional fluid irrigation capability has been disclosed. While the invention has been described with reference to a specific embodiment, the description is illustrative of the invention and is not to be construed as limiting the invention. Various modifications and applications may occur to those who are skilled in the art, without departing from the true spirit and scope of the invention, as described by the appended claims.

What is claimed is:

1. A medical ablation device system comprising:
   (a) an elongate tubular element having a distal section, a distal end, a proximal end, and at least one lumen extending therebetween, wherein an opening is located at one side of the distal section;
   (b) an inner tubing located within the lumen of the elongate tubular element, the inner tubing having a distal section, a distal end, a proximal end, and a lumen extending therebetween, wherein a deployable electrode is located at the distal section of the inner tubing, the deployable electrode comprising a pre-shaped extendible electrode that stays within the lumen of the elongate tubular element under a non-deployed state and extends out of the elongate tubular element through said opening during a deployment state;
   (c) a handle attachably secured at the proximal end of the tubular element, the handle having a cavity;
   (d) an external RF energy generator having a conducting wire, wherein the energy is supplied to the deployable electrode through the conducting wire; and
   (e) means for generating rotational motion for the distal section of the elongate tubular element, the means comprising a motor mounted in the cavity of the handle, which has a rotatable motor shaft, an elongate connecting shaft having a first end to which the proximal end of the elongate tubular element is connected, and a second end connected to the motor, so that when the motor shaft rotates, the elongate tubular element also rotates.

2. The medical ablation device system as in claim 1 further comprising a temperature sensor, wherein the temperature sensor is located at the distal section of the medical ablation device system.

3. The medical ablation device system as in claim 2 further comprising a temperature controller, wherein the temperature measured from the temperature sensor is relayed to the temperature controller adapted to effect the energy supply of the RF energy generator.

4. The medical ablation device system of claim 1, wherein the extendible electrode is selected from the group consisting of platinum, iridium, gold, silver, stainless steel, Nitinol, and an alloy of their mixtures.

5. The medical ablation device system of claim 1, wherein the electrode is selected from the group consisting of a curved plate, a plurality of curved wires, a curved plate with studded surface, a plurality of coils, and a meshed plate.

6. The medical ablation device system as in claim 1 further comprising a hollow passage within the lumen of the inner tubing, a fluid inlet port at the proximal end portion of the inner tubing, wherein the hollow passage is to provide fluid communication and flow of fluid originating from the fluid inlet port through the opening to portions of the exterior surface of the extendible electrode which direct the fluid flow from inside the inner tubing over the exterior surface to provide a fluid protective layer surrounding the extendible electrode to minimize temperature elevation of the extendible electrode in contact with biological tissues.

7. The medical ablation device system of claim 6, wherein the fluid is selected from the group consisting of heparin solution, saline solution, fluoroquinolone, lactic acid, glycolic acid, alpha hydroxy organic acids, vitamins, povidone-iodine, nitrate compounds, virucidal agents, anti-ulcer agents, anti-inflammatory agents, antibiotics, and their mixtures.

* * * * *